United States Patent
Burton et al.

(10) Patent No.: US 10,115,575 B2
(45) Date of Patent: Oct. 30, 2018

(54) PROBABILITY-BASED LIBRARY SEARCH ALGORITHM (PROLS)

(71) Applicant: DH Technologies Development Pte. Ltd., Singapore (SG)

(72) Inventors: Lyle Lorrence Burton, Woodbridge (CA); Gordana Ivosev, Etobicoke (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/576,875

(22) PCT Filed: May 26, 2016

(86) PCT No.: PCT/IB2016/053100
§ 371 (c)(1),
(2) Date: Nov. 27, 2017

(87) PCT Pub. No.: WO2016/203328
PCT Pub. Date: Dec. 22, 2016

(65) Prior Publication Data
US 2018/0166264 A1    Jun. 14, 2018

Related U.S. Application Data

(60) Provisional application No. 62/181,624, filed on Jun. 18, 2015.

(51) Int. Cl.
*H01J 49/04* (2006.01)
*H01J 49/00* (2006.01)
*G06F 19/00* (2018.01)

(52) U.S. Cl.
CPC ........ *H01J 49/0036* (2013.01); *G06F 19/709* (2013.01); *H01J 49/0072* (2013.01)

(58) Field of Classification Search
CPC ............... H01J 49/0027; H01J 49/0031; H01J 49/0036; H01J 49/0072; H01J 49/004; H01J 49/0045; G06F 19/70; G06F 19/709
See application file for complete search history.

(56) References Cited

U.S. PATENT DOCUMENTS

2007/0282537 A1 * 12/2007 Freitas .................... G06F 19/22
                                                                  702/19
2010/0179766 A1 *  7/2010 Kim .................... G01N 33/6848
                                                                  702/19
(Continued)

FOREIGN PATENT DOCUMENTS

JP      4918846 B2    4/2012
WO    2014045093 A1    3/2014

OTHER PUBLICATIONS

International Search Report and Written Opinion for PCT/IB2016/053100, dated Sep. 9, 2016.

*Primary Examiner* — David E Smith
(74) *Attorney, Agent, or Firm* — John R. Kasha; Kelly L. Kasha; Kasha Law LLC

(57) ABSTRACT

One or more known compounds of a sample are ionized. At least one precursor ion corresponding to a compound of the one or more known compounds is selected and fragmented, producing a product ion mass spectrum for the precursor ion. An m/z tolerance probability function that varies from 1 to 0 with increasing values of an m/z difference between two mass peaks and that includes one or more values between 1 and 0 is received. A library product ion mass spectrum for the at least one compound is retrieved from a memory. An m/z difference between at least one experimental product ion mass peak in the product ion mass spectrum and at least one library product ion mass peak in the library product ion mass spectrum is calculated. An m/z tolerance probability that determines if the two peaks are corresponding peaks is (Continued)

calculated from the m/z difference using the probability function.

15 Claims, 14 Drawing Sheets

(56) References Cited

U.S. PATENT DOCUMENTS

| | | |
|---|---|---|
| 2011/0288779 A1 | 11/2011 | Satulovsky |
| 2012/0191685 A1* | 7/2012 | Albar Ramirez .. G01N 33/6848 707/706 |
| 2014/0252218 A1 | 9/2014 | Wright et al. |
| 2015/0144778 A1 | 5/2015 | Bonner et al. |

* cited by examiner

PROBABILITY-BASED LIBRARY SEARCH ALGORITHM (PROLS)

CROSS REFERENCE TO RELATED APPLICATION

This application claims the benefit of U.S. Provisional Patent Application Ser. No. 62/181,624, filed Jun. 18, 2015, the content of which is incorporated by reference herein in its entirety.

INTRODUCTION

Various embodiments relate generally to tandem mass spectrometry. More particularly various embodiments relate to systems and methods for comparing an experimental product ion spectrum to a known library product ion spectrum in order to identify a compound or confirm the presence of a compound in an experimental sample.

In many mass spectrometry applications, library searching is used to identify an unknown compound or to confirm the presence of a suspected compound. This is done by comparing the mass spectrometry/mass spectrometry (MS/MS), or product ion, mass spectrum of a pure standard (the 'library' spectrum) with an experimental mass spectrum (the "unknown" spectrum).

A number of different algorithms have been published which produce a similarity score between the two spectra, the most common being a dot-product approach. This dot-product approach treats each product ion spectrum as a vector in a multi-dimensional space (the dimensions being the m/z values present in the spectra) and takes the cosine of the angle between them.

This approach works well, at least for low resolution mass spectra. However, in order to be applied it is necessary to "align" the product ion mass spectra so that common m/z values between the spectra are treated as the same feature or "dimension." For example, if one spectrum has a peak at m/z 100.2 Da and the other has a peak at m/z 100.4 Da, do they represent the same feature (with 0.2 Da measurement error) or two different features? These algorithms were originally developed for quadrupole instrumentation and the universal approach taken was to work at nominal mass allowing for an exact comparison of the integer m/z. For accurate mass spectra it is necessary to introduce a mass tolerance which depends on the instrument type and quality of the calibration. If two m/z values are within this mass tolerance, they are assumed to represent the same feature, otherwise not. One problem with using a specific mass tolerance (in either Da or ppm) is that setting it correctly is critical. If set optimistically (often the case), identical features which are just outside the tolerance are not properly aligned; if set pessimistically, what are actually different features are considered to be the same. With the traditional dot-product algorithm, peak intensities are used directly when calculating the cosine (possibly after a transformation such as taking a square root or weighting by m/z). These algorithms were originally developed for electron impact (EI) ionization sources with very reproducible intensity patterns. Since relative intensities are less consistent with electro-spray ionization (ESI), a "fudge factor" can be introduced, which adjusts the relative intensity of a peak in one spectrum to be identical to that of the corresponding peak in the other, provided that the two relative intensities are initially within some factor of one another (say one is less than 5× larger or smaller than the other).

A serious problem with this approach is that the reported library score can change significantly with even small changes to one of the spectra. For example, consider a library spectrum with a peak with an intensity of 1 and a tolerance factor of 5×.

If the intensity of the corresponding peak in an unknown spectrum is 4.9, its intensity gets reset to 1 and a good match is obtained (at least for this one peak); if the intensity were 5.1 (a small difference), it would remain unchanged and a much poorer match would be obtained.

As a result, in comparing experimental and library product ion mass spectra, the mass spectrometry industry currently (1) lacks systems and methods for optimally setting the mass tolerance used in the comparison, and (2) lacks systems and methods for optimally adjusting the relative intensities of experimental product ion peaks used in the comparison.

SUMMARY

A system is disclosed for determining corresponding mass peaks in experimental and library product ion spectra using a mass-to-charge ratio (m/z) tolerance probability function with values between 1 and 0. The system includes an ion source, a tandem mass spectrometer, and a processor.

The ion source ionizes one or more known compounds of a sample, producing an ion beam of precursor ions. The tandem mass spectrometer receives the ion beam from the ion source. The tandem mass spectrometer selects at least one precursor ion from the ion beam corresponding to at least one compound of the one or more known compounds and fragments the at least one precursor ion, producing a product ion mass spectrum for the at least one precursor ion.

The processor performs a number of steps. The processor receives the product ion mass spectrum from the tandem mass spectrometer. The processor receives an m/z tolerance probability function that varies from 1 to 0 with increasing values of an m/z difference between two mass peaks and that includes one or more values between 1 and 0. The processor retrieves from a memory a library product ion mass spectrum for the at least one compound. The processor calculates an m/z difference between at least one experimental product ion mass peak in the product ion mass spectrum and at least one library product ion mass peak in the library product ion mass spectrum. The processor calculates an m/z tolerance probability, $(p_{m/z})_1$, from the m/z difference using the m/z tolerance probability function. The processor determines if the at least one experimental product ion mass peak and the at least one library product ion mass peak are corresponding peaks based on the m/z tolerance probability, $(p_{m/z})_1$.

A method is disclosed for determining corresponding mass peaks in experimental and library product ion spectra using an m/z tolerance probability function with values between 1 and 0. One or more known compounds of a sample are ionized using an ion source, producing an ion beam of precursor ions. The ion beam are received from the ion source, at least one precursor ion is selected from the ion beam corresponding to at least one compound of the one or more known compounds, and the at least one precursor ion is fragmented using a tandem mass spectrometer, producing a product ion mass spectrum for the at least one precursor ion.

The product ion mass spectrum is received from the tandem mass spectrometer using a processor. An m/z tolerance probability function that varies from 1 to 0 with increasing values of an m/z difference between two mass peaks and that includes one or more values between 1 and 0 is received using the processor. A library product ion mass spectrum for the at least one compound is retrieved from a memory using the processor. An m/z difference between at least one experimental product ion mass peak in the product ion mass spectrum and at least one library product ion mass peak in the library product ion mass spectrum is calculated using the processor. An m/z tolerance probability, $(p_{m/z})_1$, is calculated from the m/z difference using the m/z tolerance probability function using the processor. It is determined if the at least one experimental product ion mass peak and the at least one library product ion mass peak are corresponding peaks based on the m/z tolerance probability, $(p_{m/z})_1$, using the processor.

A computer program product is disclosed that includes a non-transitory and tangible computer-readable storage medium whose contents include a program with instructions being executed on a processor so as to perform a method for determining corresponding mass peaks in experimental and library product ion spectra using an m/z tolerance probability function with values between 1 and 0.

In various embodiments, the method includes providing a system, wherein the system comprises one or more distinct software modules, and wherein the distinct software modules comprise a measurement module and an analysis module.

The measurement module receives a product ion mass spectrum from a tandem mass spectrometer. One or more known compounds of a sample are ionized using an ion source, producing an ion beam of precursor ions. The tandem mass spectrometer receives the ion beam from the ion source, selects at least one precursor ion from the ion beam corresponding to at least one compound of the one or more known compounds, and fragments the at least one precursor ion, producing the product ion mass spectrum for the at least one precursor ion.

The analysis module receives an m/z tolerance probability function that varies from 1 to 0 with increasing values of an m/z difference between two mass peaks and that includes one or more values between 1 and 0. The analysis module retrieves from a memory a library product ion mass spectrum for the at least one compound. The analysis module calculates an m/z difference between at least one experimental product ion mass peak in the product ion mass spectrum and at least one library product ion mass peak in the library product ion mass spectrum. The analysis module calculates an m/z tolerance probability, $(p_{m/z})_1$, from the m/z difference using the m/z tolerance probability function. The analysis module determines if the at least one experimental product ion mass peak and the at least one library product ion mass peak are corresponding peaks based on the m/z tolerance probability, $(p_{m/z})_1$.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
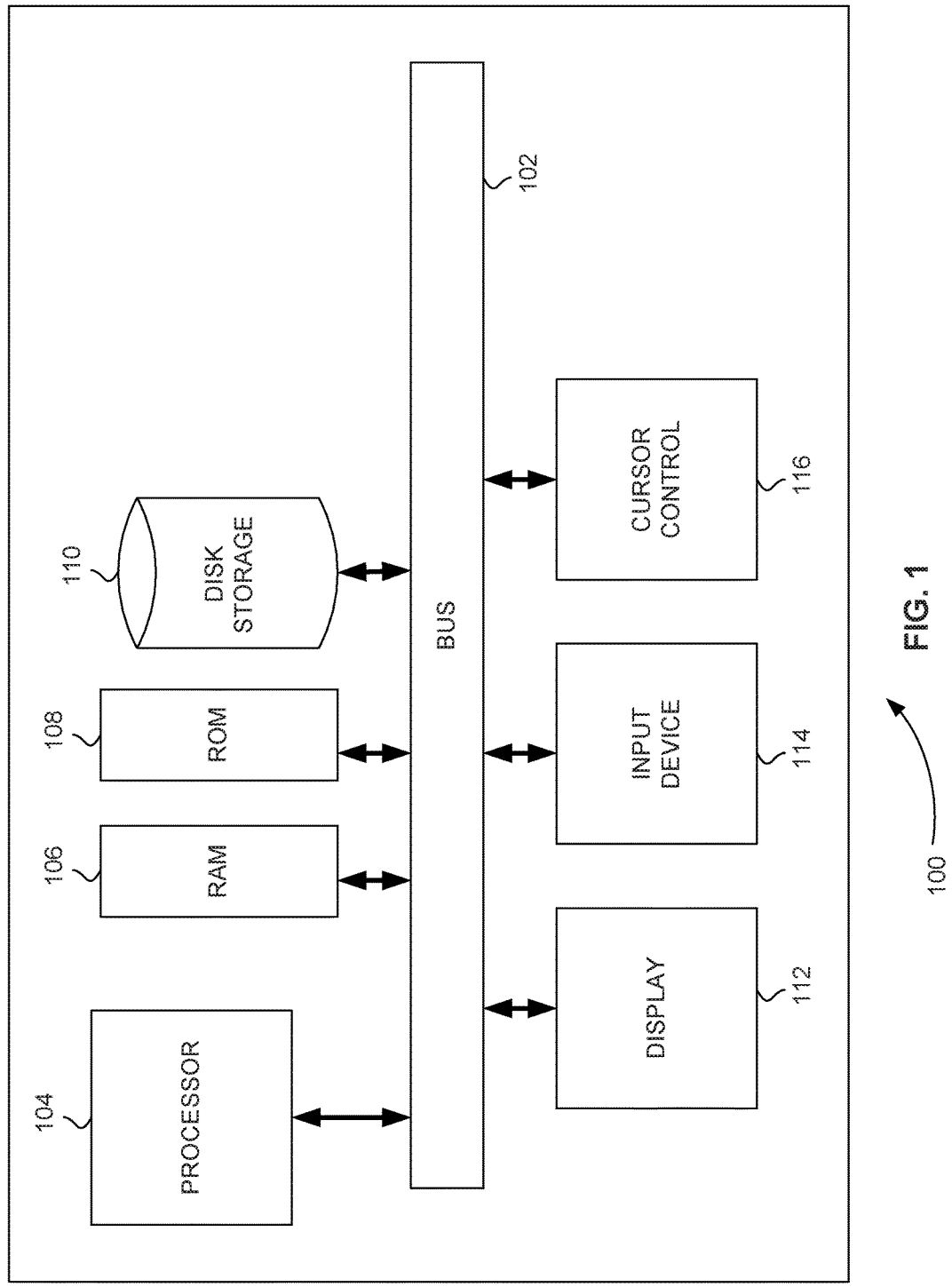
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed.

Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Probability Function with Values Between 1 and 0

As described above, in comparing experimental and library product ion mass spectra, the mass spectrometry industry currently (1) lacks systems and methods for optimally setting the mass tolerance used in the comparison, and (2) lacks systems and methods for optimally adjusting the relative intensities of experimental product ion peaks used in the comparison.

Figure 2:
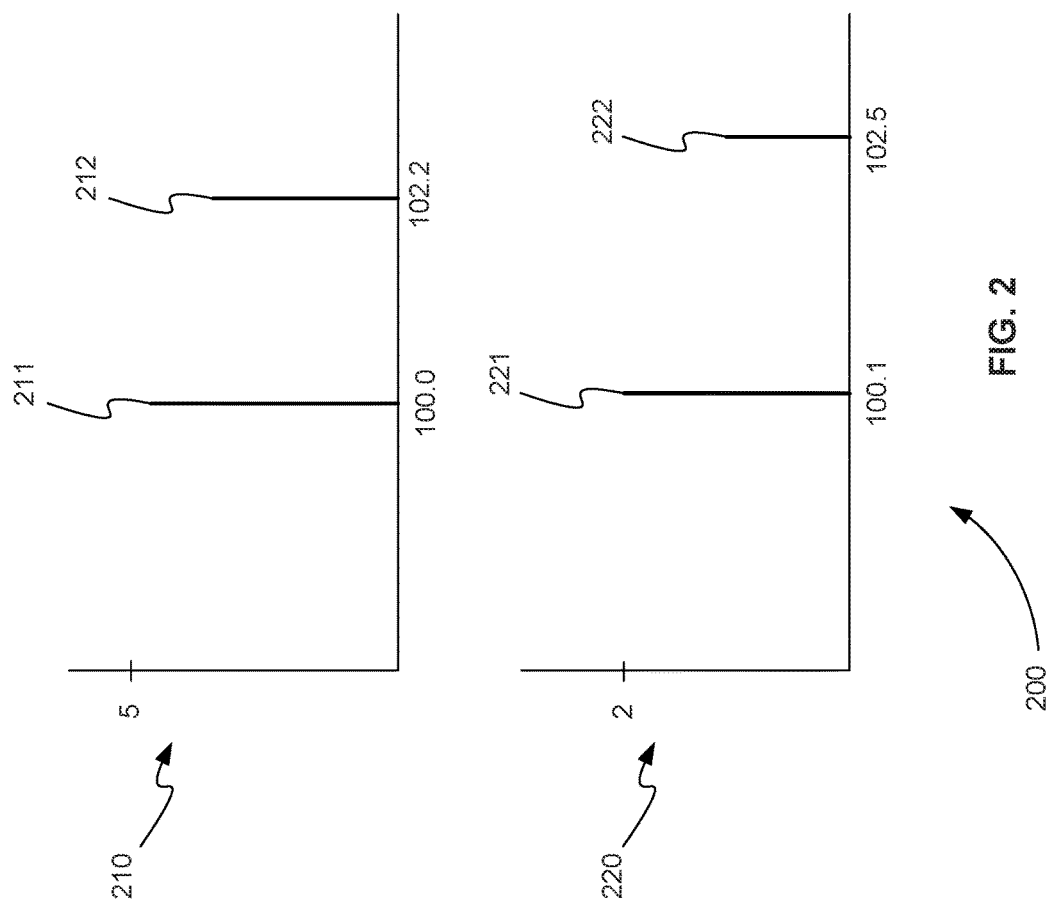
FIG. 2 is an exemplary alignment of an experimentally produced product ion mass spectrum and a library product ion mass spectrum, in accordance with various embodiments.

FIG. 2 is an exemplary alignment 200 of an experimentally produced product ion mass spectrum 210 and a library product ion mass spectrum 220, in accordance with various embodiments. Experimentally produced product ion mass spectrum 210 and library product ion mass spectrum 220 each include only two mass peaks for demonstration purposes only. Generally, the experimentally produced product ion mass spectrum and the library product ion mass spectrum include many more product ion mass peaks.

The comparison of mass peaks in experimentally produced product ion mass spectrum 210 and library product ion mass spectrum 220 is dependent on the specific mass-to-charge ratio (m/z) tolerance used. For example, if the m/z tolerance is 0.2, then mass peak 211 (m/z=100.0) and 221 (m/z=100.1) are treated as the same feature or dimension, and mass peak 212 (m/z=102.2) and 222 (m/z=102.5) are treated as different features or dimensions. If, however, the m/z tolerance is 0.4, then mass peak 211 (m/z=100.0) and 221 (m/z=100.1) are treated as the same feature or dimension, and mass peak 212 (m/z=102.2) and 222 (m/z=102.5)

as the same feature or dimension. Note that one skilled in the art can appreciate that mass and m/z are used interchangeable in discussing mass spectra, converting mass to m/z is just a matter of dividing mass by charge (z), and converting m/z to mass is just a matter of multiplying m/z by charge (z).

Conventional m/z Tolerance

Conventionally, the m/z tolerance is a cutoff value, which is a discontinuous function or a step function. For example, all mass peaks that have m/z values within the cutoff are the same feature or dimension. All mass peaks that have m/z values outside the cutoff are different features or dimensions.

Figure 3:
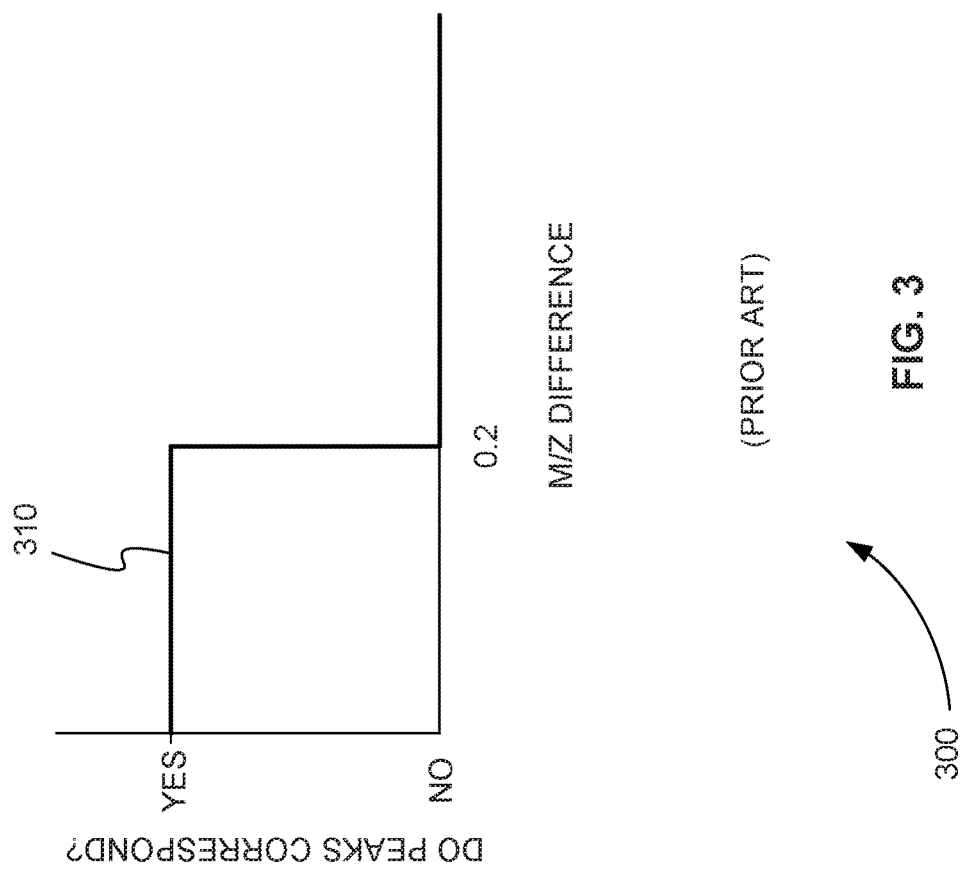
FIG. 3 is an exemplary plot of a conventional mass-to-charge ratio (m/z) tolerance function with a cutoff value of 0.2 m/z.

FIG. 3 is an exemplary plot 300 of a conventional m/z tolerance function 310 with a cutoff value of 0.2 m/z. Plot 300 of m/z tolerance function 310 shows that when the m/z difference between a mass peak in the experimentally produced product ion mass spectrum and a mass peak in the library product ion mass spectrum is between 0 and 0.2 m/z, the mass peaks in the different spectra are treated as the same feature or dimension or are treated as corresponding peaks. In addition, m/z tolerance function 310 shows that when the m/z difference between a mass peak in the experimentally produced product ion mass spectrum and a mass peak in the library product ion mass spectrum is greater than 0.2 m/z, the mass peaks in the different spectra are treated as different features or dimensions.

Returning to FIG. 2, an experimentally produced product ion mass spectrum, such as spectrum 210, is compared to a library product ion mass spectrum, such as spectrum 220, using a dot-product algorithm. A dot-product algorithm is highly dependent on the number of separate features or dimensions in the two spectra. A dot-product algorithm is, therefore, highly dependent on the m/z tolerance selected.

Figure 4:
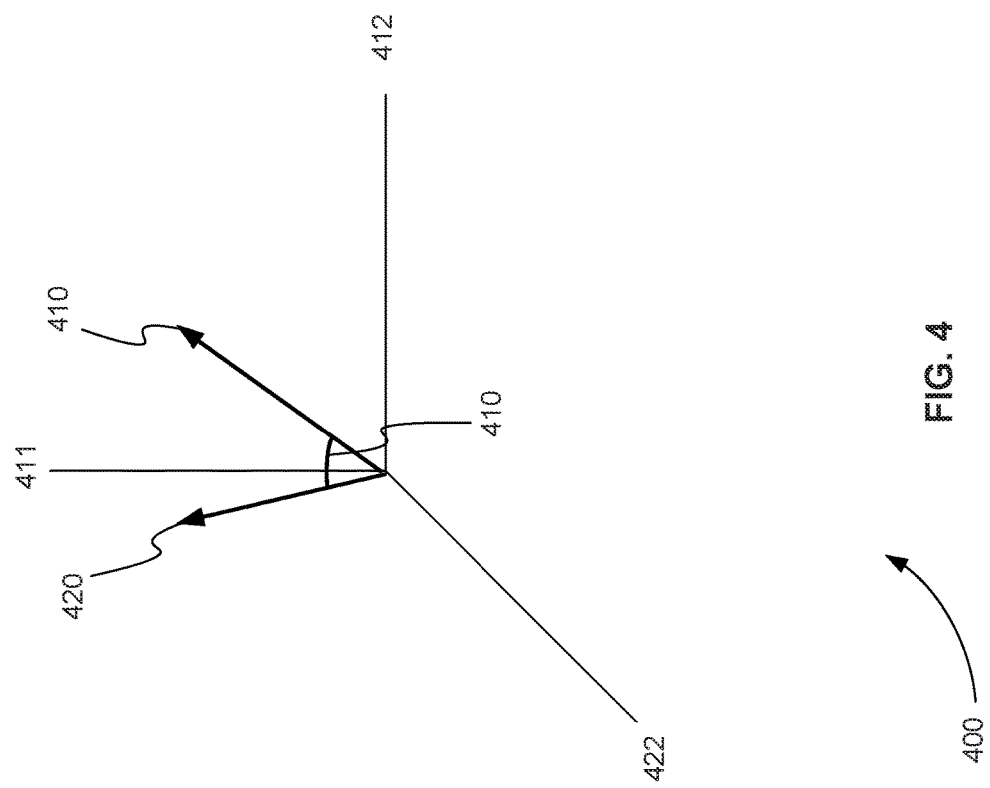
FIG. 4 is an exemplary diagram of how a dot-product is graphically generated from the spectra of FIG. 2 and the m/z tolerance function of FIG. 3.

FIG. 4 is an exemplary diagram 400 of how a dot-product is graphically generated from the spectra of FIG. 2 and the m/z tolerance function of FIG. 3. The m/z tolerance function of FIG. 3 has an m/z cutoff value of 0.2 m/z. As described above, when the m/z tolerance is 0.2 m/z, the spectra of FIG. 2 are treated as having three separate features or dimensions. A first dimension 411 of FIG. 4 represents features including mass peak 211 of experimentally produced product ion mass spectrum 210 of FIG. 2 and mass peak 221 of library product ion mass spectrum 220 of FIG. 2. A second dimension 412 represents features including mass peak 212 of experimentally produced product ion mass spectrum 210 of FIG. 2. A third dimension 422 represents features including mass peak 222 of library product ion mass spectrum 220 of FIG. 2.

Vector 410 in FIG. 4 represents experimentally produced product ion mass spectrum 210 of FIG. 2. Note that vector 410 only resides in the plane formed by first dimension 411 and second dimension 412. This is because experimentally produced product ion mass spectrum 210 of FIG. 2 has no mass peak corresponding to mass peak 22 of library product ion mass spectrum 220 of FIG. 2 when the m/z tolerance is 0.2.

Vector 420 in FIG. 4 represents library product ion mass spectrum 220 of FIG. 2. Note that vector 420 only resides in the plane formed by first dimension 411 and third dimension 422. This is because library product ion mass spectrum 220 of FIG. 2 has no mass peak corresponding to mass peak 212 of experimentally produced product ion mass spectrum 210 of FIG. 2 when the m/z tolerance is 0.2.

Note that vectors 410 and 420 of FIG. 4 are plotted directly from the peak intensities of experimentally produced product ion mass spectrum 210 and library product ion mass spectrum 220 of FIG. 2. As described above, this works well for electron ionization (EI), but not for electrospray ionization (ESI).

The dot-product of vectors 410 and 420 is the product of their magnitudes or lengths multiplied by the cosine of angle 430. Conventionally, a library score or purity score is calculated for the dot-product of two spectra using:

$$\text{score} = 100\% \times \frac{\left(\sum U_i L_i\right)^2}{\sum U_i U_i \times \sum L_i L_i}$$

where $U_i$ is the intensity of ith unknown or experimental peak and $L_i$ is the intensity of ith library peak. Note that as described above, for ESI the library intensities are after any adjustment using a "fudge factor" or weighting. The $U_i L_i$ summation takes place using only peaks common between the two spectra. The other summations in the library score equation use all unknown and library peaks respectively.

Returning to FIG. 2, if the m/z tolerance is 0.2, then mass peak 211 (m/z=100.0) and 221 (m/z=100.1) are treated as the same feature or dimension, and mass peak 212 (m/z=102.2) and 222 (m/z=102.5) are treated as different features or dimensions. The intensity of mass peak 211 is 4.8, the intensity of mass peak 212 is 4.0, the intensity of mass peak 221 is 2.0, and the intensity of mass peak 222 is 1.2. The library score is then calculated as:

$$\text{score} = 100\% \times \frac{(4.8 \times 2.0)^2}{(4.8 \times 4.8 + 4.0 \times 4.0) \times (2.0 \times 2.0 + 1.2 \times 1.2)} = 43\%.$$

This library score uses the actual peak intensities. Again, for ESI the peak intensities are often modified before calculating the library score.

Figure 5:
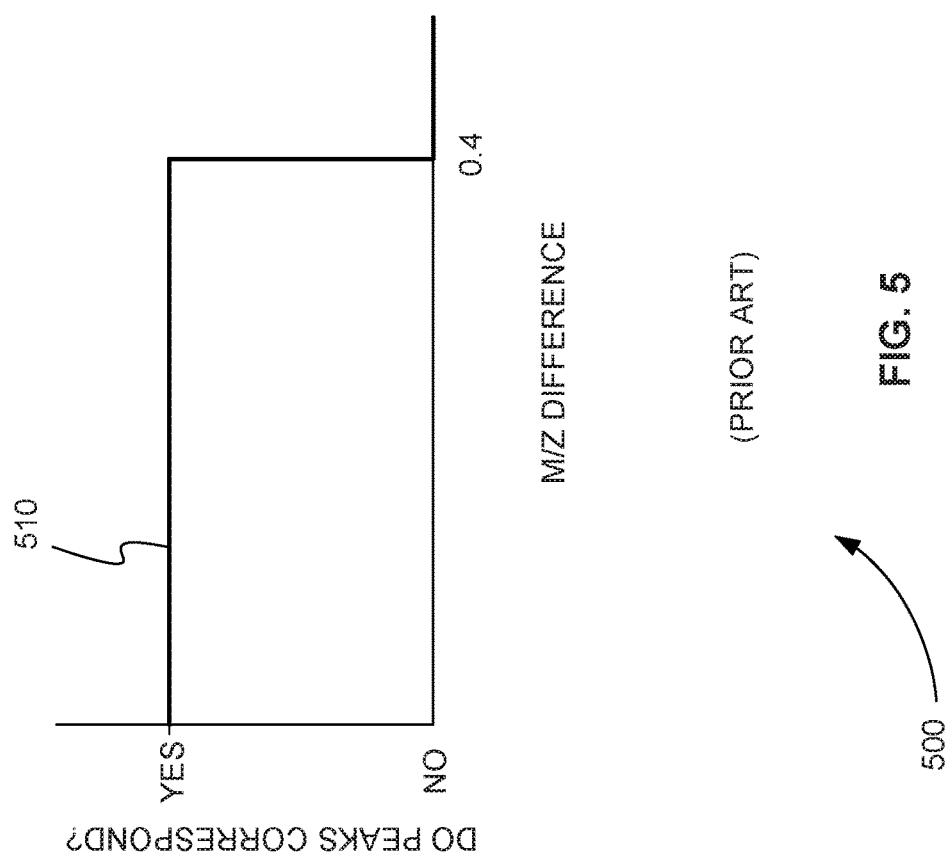
FIG. 5 is an exemplary plot of a conventional m/z tolerance function with a cutoff value of 0.4 m/z.
Figure 6:
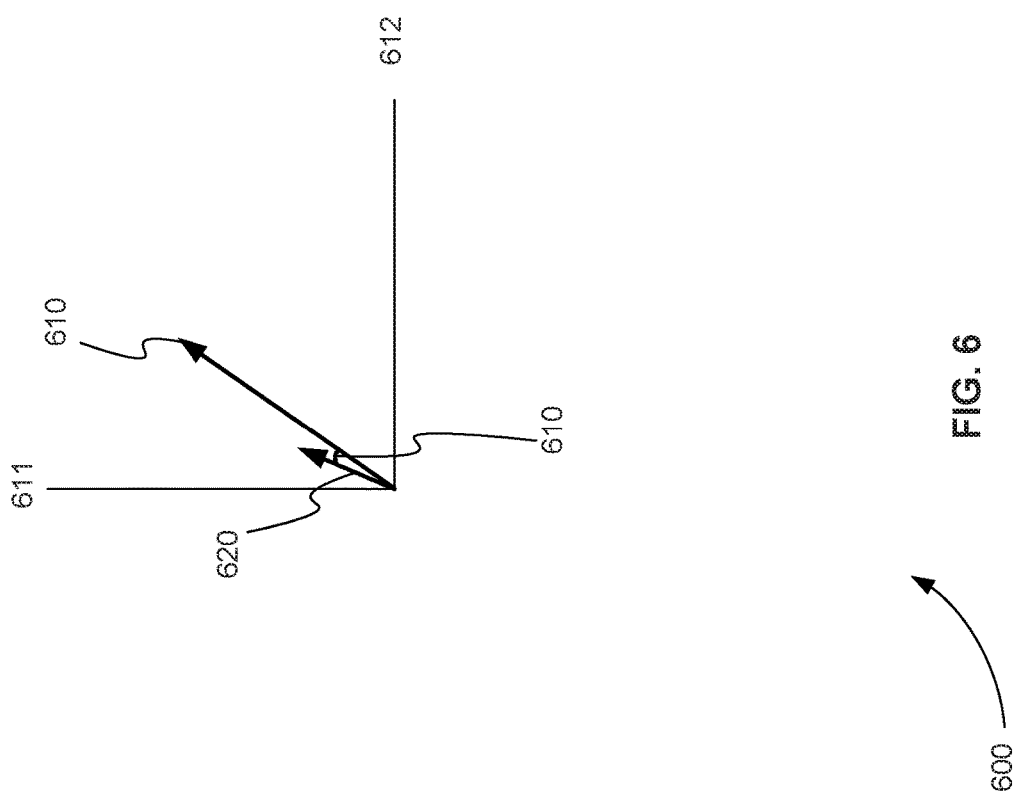
FIG. 6 is an exemplary diagram of how a dot-product is graphically generated from the spectra of FIG. 2 and the m/z tolerance function of FIG. 5.

FIG. 5 is an exemplary plot 500 of a conventional m/z tolerance function 510 with a cutoff value of 0.4 m/z. Plot 500 of m/z tolerance function 510 shows that when the m/z difference between a mass peak in the experimentally produced product ion mass spectrum and a mass peak in the library product ion mass spectrum is between 0 and 0.4 m/z, the mass peaks in the different spectra are treated as the same feature or dimension or are treated as corresponding peaks. In addition, m/z tolerance function 510 shows that when the m/z difference between a mass peak in the experimentally produced product ion mass spectrum and a mass peak in the library product ion mass spectrum is greater than 0.4 m/z, the mass peaks in the different spectra are treated as different features or dimensions. FIG. 6 is an exemplary diagram 600 of how a dot-product is graphically generated from the spectra of FIG. 2 and the m/z tolerance function of FIG. 5. The m/z tolerance function of FIG. 5 has an m/z cutoff value of 0.4 m/z. As described above, when the m/z tolerance is 0.4 m/z, the spectra of FIG. 2 are treated as have just two separate features or dimensions. A first dimension 611 of FIG. 6 represents features including mass peak 211 of experimentally produced product ion mass spectrum 210 of FIG. 2 and mass peak 221 of library product ion mass spectrum 220 of FIG. 2. A second dimension 612 represents features including mass peak 212 of experimentally produced product ion mass spectrum and mass peak 222 of library product ion mass spectrum 220 of FIG. 2.

Vector 610 in FIG. 6 represents experimentally produced product ion mass spectrum 210 of FIG. 2. Vector 620 in FIG. 6 represents library product ion mass spectrum 220 of FIG. 2. Note that vector 610 and vector 620 reside in the same plane.

Returning to FIG. 2, if the m/z tolerance is 0.4, then mass peak 211 (m/z=100.0) and 221 (m/z=100.1) are treated as the same feature or dimension, and mass peak 212 (m/z=102.2) and 222 (m/z=102.5) are also treated as the same feature or dimension. The intensity of mass peak 211 is 4.8, the intensity of mass peak 212 is 4.0, the intensity of mass peak 221 is 2.0, and the intensity of mass peak 222 is 1.2. The library score is then calculated as:

$$\text{score} = 100\% \times \frac{(4.8 \times 2.0 + 4.0 \times 1.2)^2}{(4.8 \times 4.8 + 4.0 \times 4.0) \times (2.0 \times 2.0 + 1.2 \times 1.2)} = 98\%.$$

Note also that vectors 610 and 620 of FIG. 6 are plotted directly from the peak intensities of experimentally produced product ion mass spectrum 210 and library product ion mass spectrum 220 of FIG. 2. As described above, this works well for electron ionization (EI), but not for electrospray ionization (ESI).

A comparison of FIGS. 4 and 6 shows how differently the dot-product is calculated for the spectra of FIG. 2 depending on the m/z tolerance used. In FIG. 4, the dot-product is calculated in a three-dimensional space. In FIG. 6, the dot-product is calculated in a two-dimensional space. The library scores are also quite different as shown above.

Conventional Intensity Ratio Threshold

The dot-product calculation also depends on the intensity ratio adjustment when ionization methods such as ESI are used. As described above, ESI provides less consistent peak intensities across experiments than techniques such as EI. In general, all intensities are relative. In other words, the largest peak in a product ion spectrum is usually taken as 100% (or some other constant value). The idea is that the comparison should not be influenced by the total amount of a compound or analyte present in the library or unknown, just the general pattern. As a result, some dot-product calculations perform an adjustment to the intensities of one of the compared spectra based on an intensity ratio tolerance or threshold.

For example, if the intensity of an unknown peak is 4.9 and the intensity of the corresponding library peak is 1, then the ratio of intensities of the unknown peak to the library peak is 4.9. If the intensity ratio threshold is 5, then the intensity ratio of 4.9 is within this threshold. When the intensity ratio of corresponding peaks is within the intensity ratio threshold, the intensities of the two peaks are made to be the same. This is the adjustment or "fudge factor" described above. For example, the unknown peak with intensity 4.9 is treated as having an intensity of 1, which is the intensity of the corresponding library peak. When the intensity ratio of corresponding peaks is not within the intensity ratio threshold, the intensities of the corresponding peaks are left unchanged. If the intensities of the corresponding peaks vary widely and are left unchanged, the score is reduced significantly.

Therefore, this intensity ratio threshold impacts the dot-product calculated for spectra comparisons by either allowing a difference in corresponding peak intensities or not allowing a difference in corresponding peak intensities. As a result, the intensity ratio threshold acts very much like the m/z tolerance described above. It is a cutoff value for not allowing a difference in corresponding peak intensities. It is then also a discontinuous or step function.

Figure 7:
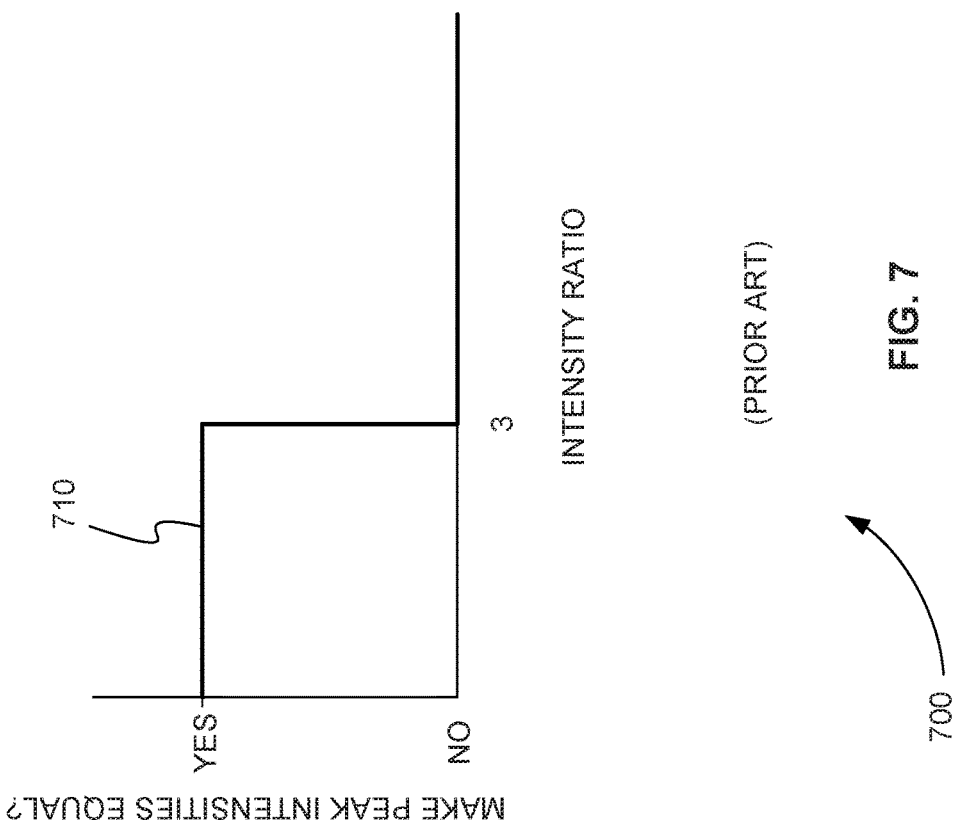
FIG. 7 is an exemplary plot of a conventional intensity ratio threshold function with a cutoff value of 3.

FIG. 7 is an exemplary plot 700 of a conventional intensity ratio threshold function 710 with a cutoff value of 3. Plot 700 of intensity ratio threshold function 710 shows that when the ratio of an intensity of a mass peak in the experimentally produced product ion mass spectrum to an intensity of a corresponding mass peak of the library product ion mass spectrum is between 1 and 3, the two mass peaks in the different spectra are treated as having the same intensity. In addition, intensity ratio threshold function 710 shows that when the ratio of an intensity of a mass peak in the experimentally produced product ion mass spectrum to an intensity of a corresponding mass peak of the library product ion mass spectrum is greater than 3, the intensities of the two mass peaks in the different spectra left unchanged.

Returning to FIG. 2, mass peak 211 of experimentally produced product ion mass spectrum 210 has an intensity of 4.8. Corresponding mass peak 221 of library product ion mass spectrum 220 has an intensity of 2. The ratio of the intensities of the two mass peaks is then 2.4. If intensity ratio threshold function 710 of FIG. 7 is used, a ratio of 2.4 is less than the cutoff ratio of 3, so mass peak 211 and mass peak 221 are treated as having the same intensity for the comparison algorithm used. Either mass peak 211 can be made to have the intensity of mass peak 221, or mass peak 221 can be made to have the intensity of mass peak 211, depending on the algorithm used.

Similarly in FIG. 2, mass peak 212 of experimentally produced product ion mass spectrum 210 has an intensity of 4.0. Corresponding mass peak 222 of library product ion mass spectrum 220 has an intensity of 1.2. The ratio of the intensities of the two mass peaks is then 3.33. If intensity ratio threshold function 710 of FIG. 7 is used, a ratio of 3.33 is greater than the cutoff ratio of 3, so the intensities of mass peak 212 and mass peak 222 are left unchanged.

m/z Tolerance Probability Function with Values Between 1 and 0

In various embodiments, the m/z tolerance used in the comparison of experimental and library product ion mass spectra is a probability function with values between 1 and 0, $p_{m/z}$. The probability function goes smoothly from 1 (good match) to 0 (no match). This is in contrast to the conventional method described above that has a hard or abrupt cutoff m/z tolerance and only has values of 1 or 0. The probability function can have many different shapes. What is most important, however, is that the probability has at least one value between 1 to 0 as the difference in m/z between peaks in the two spectra increases.

Figure 8:
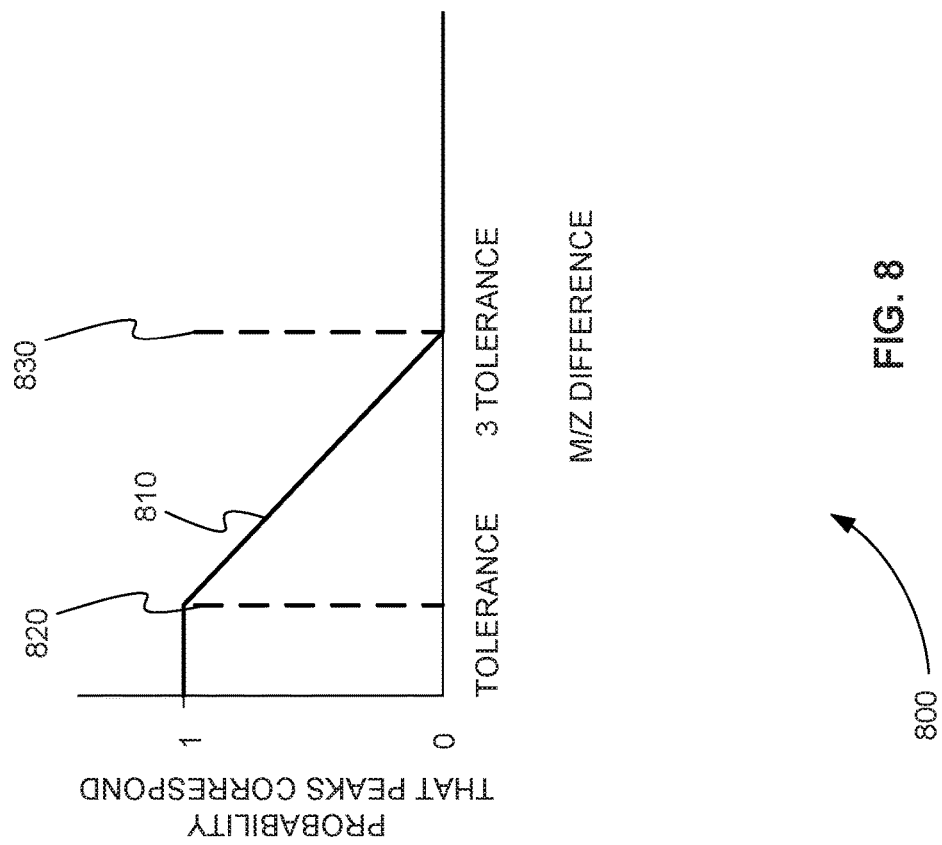
FIG. 8 is an exemplary plot of an m/z tolerance probability function with values between 1 and 0, in accordance with various embodiments.

FIG. 8 is an exemplary plot 800 of an m/z tolerance probability function 810 with values between 1 and 0, in accordance with various embodiments. Plot 800 of m/z tolerance function 810 shows that when the m/z difference between a mass peak in the experimentally produced product ion mass spectrum and a mass peak in the library product ion mass spectrum is between some m/z difference value 820 and another m/z difference value 830, the probability varies continuously from 1 to 0. In other words, in this region the probability has many values between 1 and 0. The m/z difference value 820 is, for example, an m/z tolerance value used in the conventional method. The m/z difference value 830 is, for example, a multiple of the m/z tolerance value used in the conventional method, such as 3 times the m/z tolerance value used in the conventional method.

In various embodiments, probability function 810 includes a region where the probability is 1 between an m/z difference of 0 and m/z difference value 820. Such a region is included to account for known error in the mass spectrometer measurement. For example, if you measure the same ion twice, in most cases you do not get the same m/z value. There is some error in the m/z measurement. Probability function 810 is a continuous function. In various embodiments, however, a probability function that has values between 1 and 0 can also be discontinuous.

Probability function 810 depends on m/z difference value 820, which is the cutoff tolerance value in the conventional method. Because probability function 810 includes values between 1 and 0, it is much less sensitive than the conventional method to the m/z difference value 820 being accurately set. However, the correct setting of the m/z difference value 820 still is important and cannot be completely incorrect. As a result, in various embodiments, the m/z difference value 820 is a function of the expected measurement error. The expected measurement error can be a single value based on previous experience with the mass spectrometry instrument or it can be more involved. The expected measurement error can, for example, be a probability distribution function calculated from parameters such as resolution or expected accuracy estimated from calibration peaks.

Intensity Ratio Threshold Probability Function with Values Between 1 and 0

In various embodiments, the intensity ratio threshold used in the comparison of experimental and library product ion mass spectra is also probability function with values between 1 and 0, $p_{ratio}$. The probability function, $p_{ratio}$, goes smoothly from 1 (make intensities completely the same) to 0 (do not change the intensities). This is also in contrast to the conventional method described above that has a hard or abrupt cutoff intensity ratio threshold. The probability function, $p_{ratio}$, can have many different shapes. What is most important, however, is that the probability has at least one value between 1 to 0 as the ratio of the intensities of the peaks in the two spectra increases. If the intensities are reasonably close, the intensity specific probability, $p_{ratio}$, is 1. As the difference in intensities increases and the ratio becomes larger, $p_{ratio}$ eventually falls to 0, assuming that the ratio is the larger intensity divided by the smaller intensity.

Figure 9:
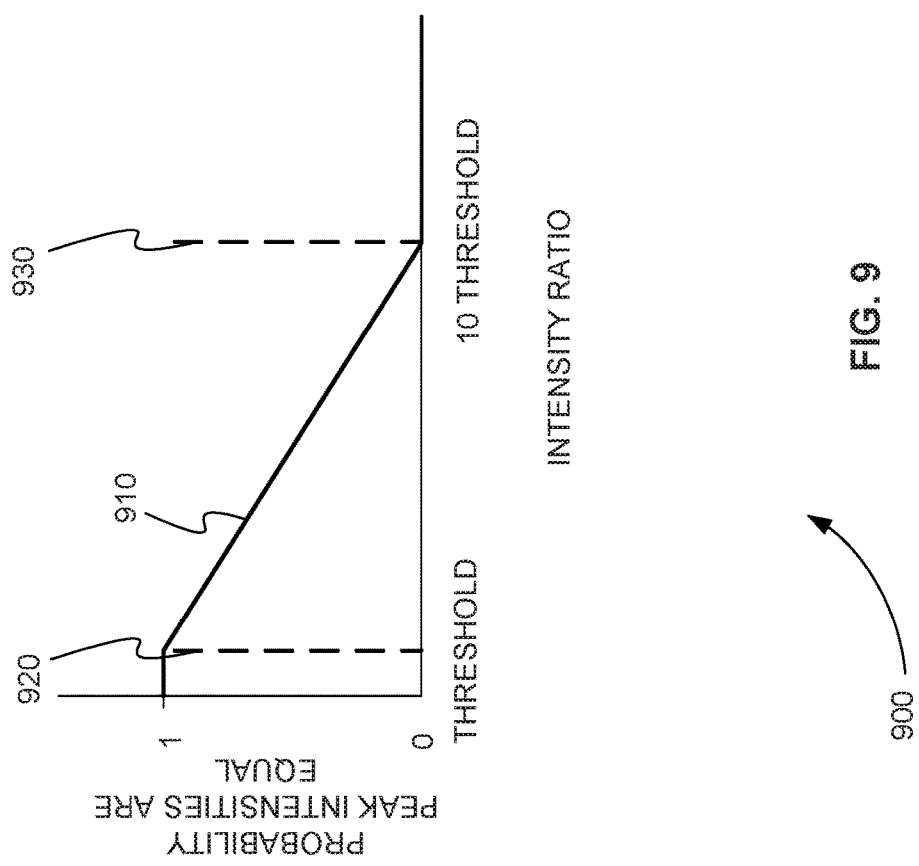
FIG. 9 is an exemplary plot of an intensity ratio threshold probability function with values between 1 and 0, in accordance with various embodiments.

FIG. 9 is an exemplary plot 900 of an intensity ratio threshold probability function with values between 1 and 0 910, in accordance with various embodiments. Plot 900 of intensity ratio threshold 910 shows that when ratio of the intensities of a peak in the experimentally produced product ion mass spectrum and a peak in the library product ion mass spectrum is between some ratio 920 and another ratio 930, the probability varies continuously from 1 to 0. In other words, in this region the probability has values between 1 and 0. The ratio 920 is, for example, an intensity ratio threshold value used in the convention method. The m/z difference value 930 is, for example, a multiple of the intensity ratio threshold value used in the convention method, such as 10 times the intensity ratio threshold value used in the convention method.

In various embodiments, probability function 910 also includes a region where the probability is 1 between a ratio of 0 and ratio 920. Such a region is included to account for known error in the mass spectrometer measurement. For example, if you measure the same ion twice, in most cases you do not get the same intensity value. There is some error in the intensity measurement.

Probabilities Used in the Comparison of Spectra

In various embodiments, an overall probability, $p_{match}$, that two peaks match is calculated from the m/z tolerance probability $p_{m/z}$ and the intensity ratio threshold probability $p_{ratio}$. The overall probability, $p_{match}$, can be calculated by combining the m/z tolerance probability $p_{m/z}$ and the intensity ratio threshold probability $p_{ratio}$ in any way. For example, $p_{match}$ can be the product of $p_{m/z}$ and $p_{ratio}$, or $$p_{match} = p_{m/z} \times p_{ratio}.$$

In various embodiments, the m/z tolerance probability $p_{m/z}$ and the intensity ratio threshold probability $p_{ratio}$ are also used in a modified form of the dot-product algorithm. A library score or purity score is calculated for this modified form of the dot-product algorithm according to:

$$\text{score} = 100\% \times \frac{\left(\sum (p_{m/z})_i U_i L_i\right)^2}{\sum U_i U_i \times \sum L_i L_i}$$

where $U_i$ is the intensity of ith unknown or experimental peak, $L_i$ is the intensity of ith library peak, and $(p_{m/z})_i$ is probability that two peaks with intensities $U_i$ and $L_i$ represent the same feature.

In various embodiments, the library score or purity score is further modified to include the intensity ratio threshold probability $p_{ratio}$. The intensity of ith library peak, $L_i$, in the library score is calculated as $$L_i = L_i + (p_{ratio})_i \times (U_i - L_i),$$

for example. As a result, when $(p_{ratio})_i$ is 1 the unknown or experimental intensity is used, and when $(p_{ratio})_i$ is 0 the library intensity is used. Note that other weighting such as taking the square roots or multiplying by the m/z can also be incorporated.

Experimental Results

A number of compounds were experimentally analyzed using a tandem mass spectrometer, and the experimental product ion spectra of the compounds were compared to product ion spectra of a library. Two separate comparisons were performed. In the first comparison, a conventional m/z tolerance cutoff value and a conventional intensity ratio threshold cutoff value were used. In the second comparison, an m/z tolerance probability function with values between 1 and 0, such as function 810 of FIG. 8, and an intensity ratio threshold probability function with values between 1 and 0, such as function 910 of FIG. 9, were used.

Figure 10:
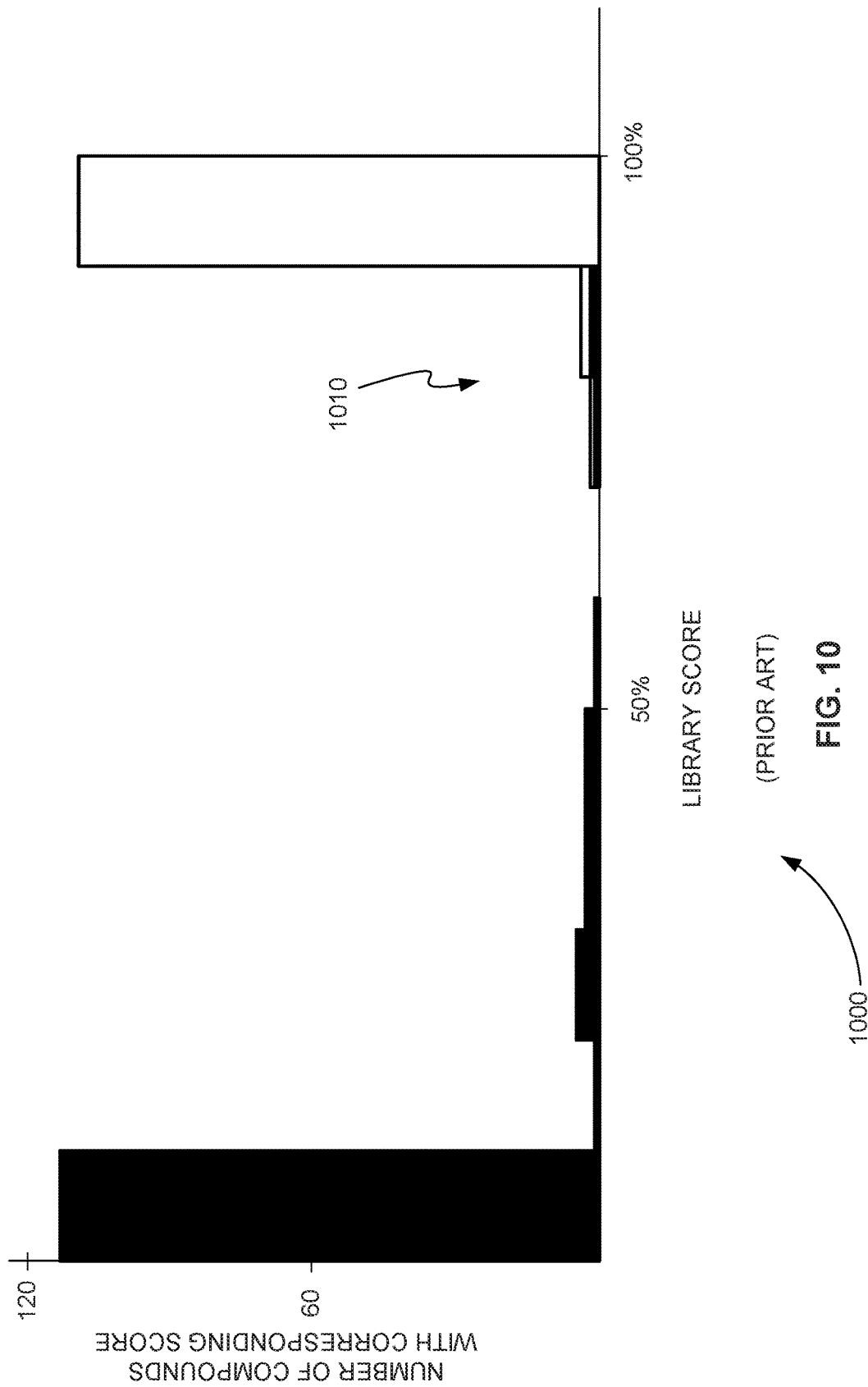
FIG. 10 is an exemplary plot of the number of compounds versus the library score of the compounds when a conventional m/z tolerance cutoff value and a conventional intensity ratio threshold cutoff value were used.

FIG. 10 is an exemplary plot 1000 of the number of compounds versus the library score of the compounds when a conventional m/z tolerance cutoff value and a conventional intensity ratio threshold cutoff value were used. The x-axis is library score (from 0% to 100%), and the y-axis represents the number of compounds with the corresponding score. The black bars are known negative compounds (which ideally would have a score of 0). The white bars are known positive compounds (which would ideally have a score of 100). FIG. 10 shows that there is an overlap region 1010 from 80% to 90% where it is not possible to distinguish true positives from false ones.

Figure 11:
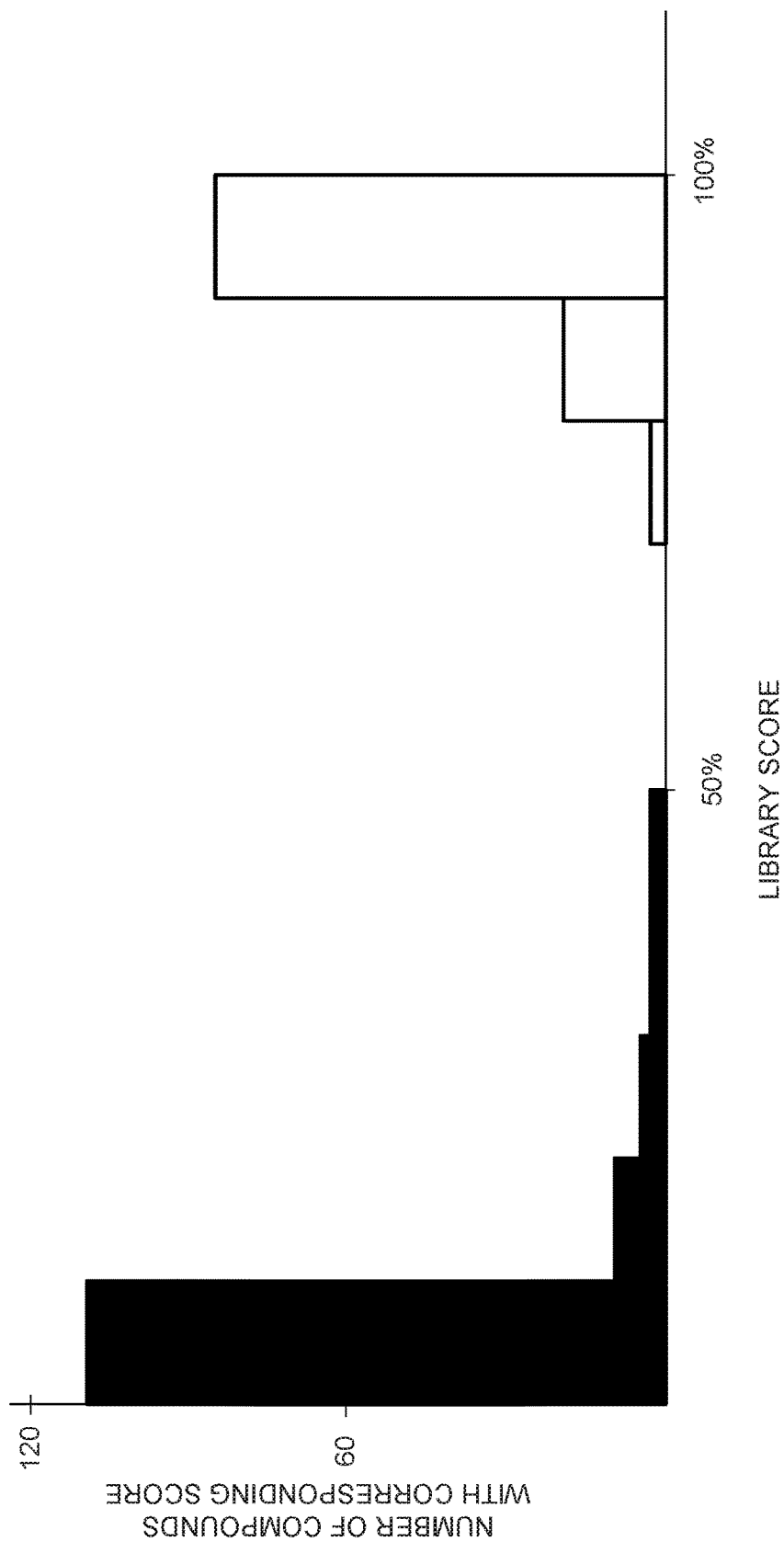
FIG. 11 is an exemplary plot of the number of compounds versus the library score of the compounds when an m/z tolerance probability function with values between 1 and 0, such as the function of FIG. 8, and an intensity ratio threshold probability function with values between 1 and 0, such as the function of FIG. 9, were used, in accordance with various embodiments.

FIG. 11 is an exemplary plot 1100 of the number of compounds versus the library score of the compounds when an m/z tolerance probability function with values between 1 and 0, such as function 810 of FIG. 8, and an intensity ratio threshold probability function with values between 1 and 0, such as function 910 of FIG. 9, were used, in accordance with various embodiments. Again, the x-axis is library score (from 0% to 100%), and the y-axis represents the number of compounds with the corresponding score. The black bars are known negative compounds (which ideally would have a score of 0). The white bars are known positive compounds (which would ideally have a score of 100).

FIG. 11 shows that when probabilities are used there are fewer true positives scoring near 100%. However, there are also fewer false negatives scoring near true ones. Comparing FIG. 10 and FIG. 11 shows that by using probabilities the true positives and false negatives are completely separated, at least for this data set. This is something the mass spectrometry industry was previously unable to obtain, except in very limited cases (i.e. small libraries).

System for Determining Corresponding Peaks

Figure 12:
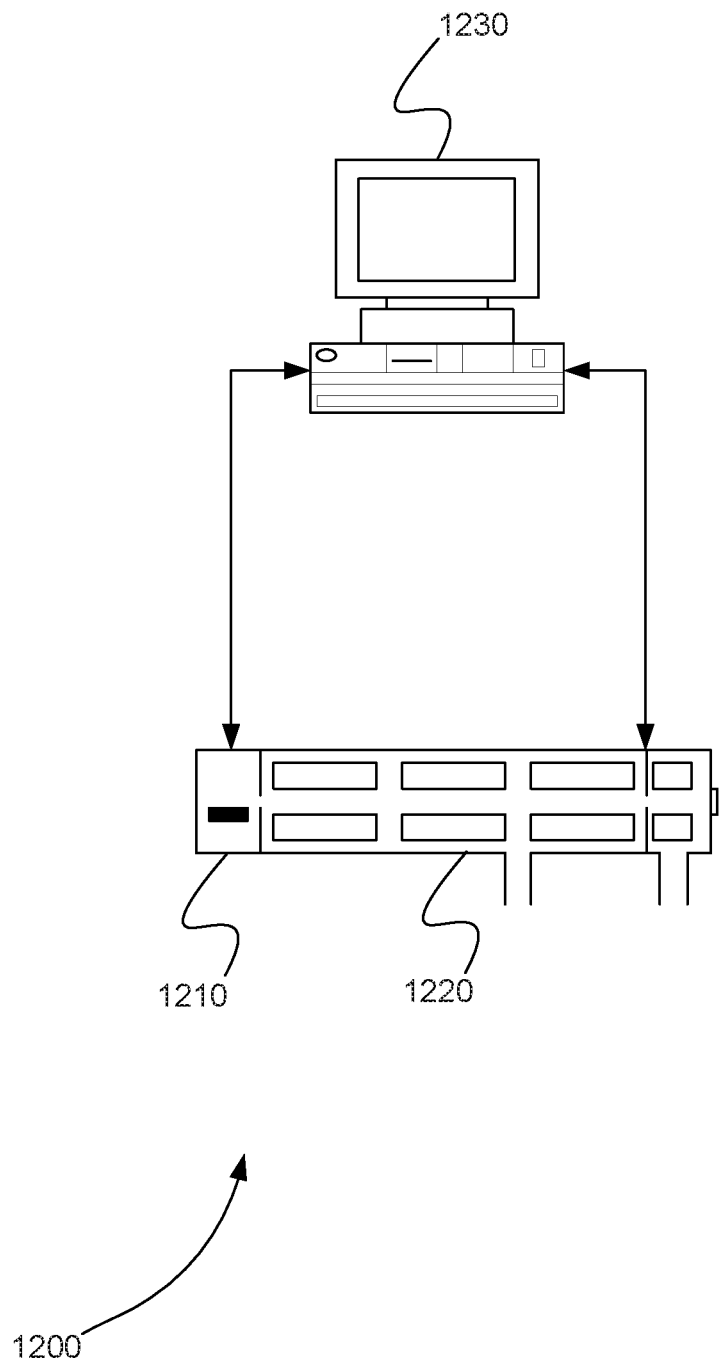
FIG. 12 is a schematic diagram of system for determining corresponding mass peaks in experimental and library product ion spectra using an m/z tolerance probability function with values between 1 and 0, in accordance with various embodiments.

FIG. 12 is a schematic diagram of system 1200 for determining corresponding mass peaks in experimental and library product ion spectra using an m/z tolerance probability function with values between 1 and 0, in accordance with various embodiments. System 1200 includes ion source 1210, tandem mass spectrometer 1220, and processor 1230. In various embodiments system 1200 can also include separation device (not shown). A separation device can separate one or more known compounds from a sample over time using a variety of techniques, for example. These techniques include, but are not limited to, ion mobility, gas chromatography (GC), liquid chromatography (LC), capillary electrophoresis (CE), or flow injection analysis (FIA).

Ion source 1210 can be part of tandem mass spectrometer 1220, or can be a separate device. Ion source 1210 ionizes one or more known compounds of a sample, producing an ion beam of precursor ions.

Tandem mass spectrometer 1220 can include, for example, one or more physical mass filters and one or more physical mass analyzers. A mass analyzer of tandem mass spectrometer 1220 can include, but is not limited to, a time-of-flight (TOF), quadrupole, an ion trap, a linear ion trap, an orbitrap, or a Fourier transform mass analyzer.

Tandem mass spectrometer 1220 receives the ion beam from ion source 1210.

Tandem mass spectrometer 1220 selects at least one precursor ion from the ion beam corresponding to at least one compound of the one or more known compounds and fragments the at least one precursor ion, producing a product ion mass spectrum for the at least one precursor ion.

Processor 1230 can be, but is not limited to, a computer, microprocessor, or any device capable of sending and receiving control signals and data from tandem mass spectrometer 1220 and processing data. Processor 1230 can be, for example, computer system 100 of FIG. 1. In various embodiments, processor 1230 is in communication with tandem mass spectrometer 1220.

Processor 1230 performs a number of steps. Processor 1230 receives the product ion mass spectrum from tandem mass spectrometer 1220. Processor 1230 receives an m/z tolerance probability function that varies from 1 to 0 with increasing values of an m/z difference between two mass peaks and that includes one or more values between 1 and 0. Processor 1230 can receive the m/z tolerance probability function directly from a user, or processor 1230 can retrieve the m/z tolerance probability function from a memory or database, for example.

The m/z tolerance probability function is predetermined, for example.

Processor 1230 retrieves from a memory a library product ion mass spectrum for the at least one compound. The memory can be an electronic or magnetic memory. In various embodiments the memory can be part of a database.

Processor 1230 calculates an m/z difference between at least one experimental product ion mass peak in the product ion mass spectrum and at least one library product ion mass peak in the library product ion mass spectrum.

Processor 1230 calculates an m/z tolerance probability, $(p_{m/z})_1$, from the m/z difference using the m/z tolerance probability function. Finally, processor 1230 determines if the at least one experimental product ion mass peak and the at least one library product ion mass peak are corresponding peaks based on the m/z tolerance probability, $(p_{m/z})_1$. Since the m/z tolerance probability, $(p_{m/z})_1$, varies from 1 to 0, any nonzero probability value indicates a level of correspondence.

In various embodiments, processor 1230 further calculates a score for a comparison of the product ion mass spectrum and the library product ion mass spectrum. Calculating the score includes calculating a product of the m/z tolerance probability, $(p_{m/z})_1$, an intensity of the at least one experimental product ion mass peak, $U_1$, and an intensity of the at least one library product ion mass peak, $L_1$.

In various embodiments, processor 1230 calculates the score using $(p_{m/z})_1$, $U_1$, and $L_1$ and any other $(p_{m/z})_i$, $U_i$, and $L_i$ according to:

$$\text{score} = 100\% \times \frac{\left(\sum (p_{m/z})_i U_i L_i\right)^2}{\sum U_i U_i \times \sum L_i L_i}$$

where $U_i$ is the intensity of ith unknown or experimental peak, $L_i$ is the intensity of ith library peak, and $(p_{m/z})_i$ is probability that two peaks with intensities $U_i$ and $L_i$ are corresponding peaks. Corresponding peaks are peaks that represent the same feature.

In various embodiments, $U_i$ and $L_i$ include a weighting factor or are transformed mathematically from the original values measured by the mass spectrometer. For example, the original measured intensity values can be weighted by multiplying them by the m/z value. Also, original measured intensity values can be transformed by taking the square root of these values, for example.

In various embodiments, processor 1230 further receives an intensity ratio threshold probability function that varies from 1 to 0 with increasing values of a ratio of intensities of two mass peaks and that includes one or more values between 1 and 0. Again, processor 1230 can receive the intensity ratio threshold probability function directly from a user, or processor 1230 can retrieve the intensity ratio threshold probability function from a memory or database, for example. The intensity ratio threshold probability function is predetermined, for example.

Processor 1230 calculates an intensity ratio from an intensity of the at least one experimental product ion mass peak and an intensity of the at least one library product ion mass peak. Processor 1230 calculates an intensity threshold probability, $(p_{ratio})_1$, from the intensity ratio using the intensity ratio threshold probability function. Finally, processor 1230 modifies an intensity, $U_1$, of the at least one experimental product ion mass peak or an intensity, $L_1$, of the at least one library product ion mass peak based on the intensity threshold probability, $(p_{ratio})_1$. For example, processor 1230 can modify the intensity, $L_1$, of the at least one library product ion mass peak according to modified $L_1 = L_1 + (p_{ratio})_1 \times (U_1 - L_1)$.

In various embodiments, processor 1230 further calculates a score for a comparison of the product ion mass spectrum and the library product ion mass spectrum using modified $L_1$, and any other modified $L_i$. The score is calculated according to:

$$\text{score} = 100\% \times \frac{\left(\sum (p_{m/z})_i U_i \text{modified} L_i\right)^2}{\sum U_i U_i \times \sum \text{modified} L_i \text{modified} L_i}$$

where $U_i$ is the intensity of ith unknown or experimental peak, $(p_{m/z})_i$ is probability that two peaks with intensities $U_i$ and $L_i$ are corresponding peaks, and modified $L_i$ is calculated according to $$\text{modified } L_i = L_i (p_{ratio})_i \times (U_i - L_i)$$

where $L_i$ is the intensity of ith library peak.

In various embodiments, processor 1230 further calculates an overall probability, $(p_{match})_1$, that the at least one experimental product ion mass peak and the at least one library product ion mass peak match. The overall probability, $(p_{match})_1$, is calculated by combining the m/z tolerance probability, $(p_{m/z})_1$, and the intensity threshold probability, $(p_{ratio})_1$. For example, $(p_{match})_1$ can be calculated as a product of $(p_{m/z})_1$ and $(p_{ratio})_1$.

Method for Determining Corresponding Peaks

Figure 13:
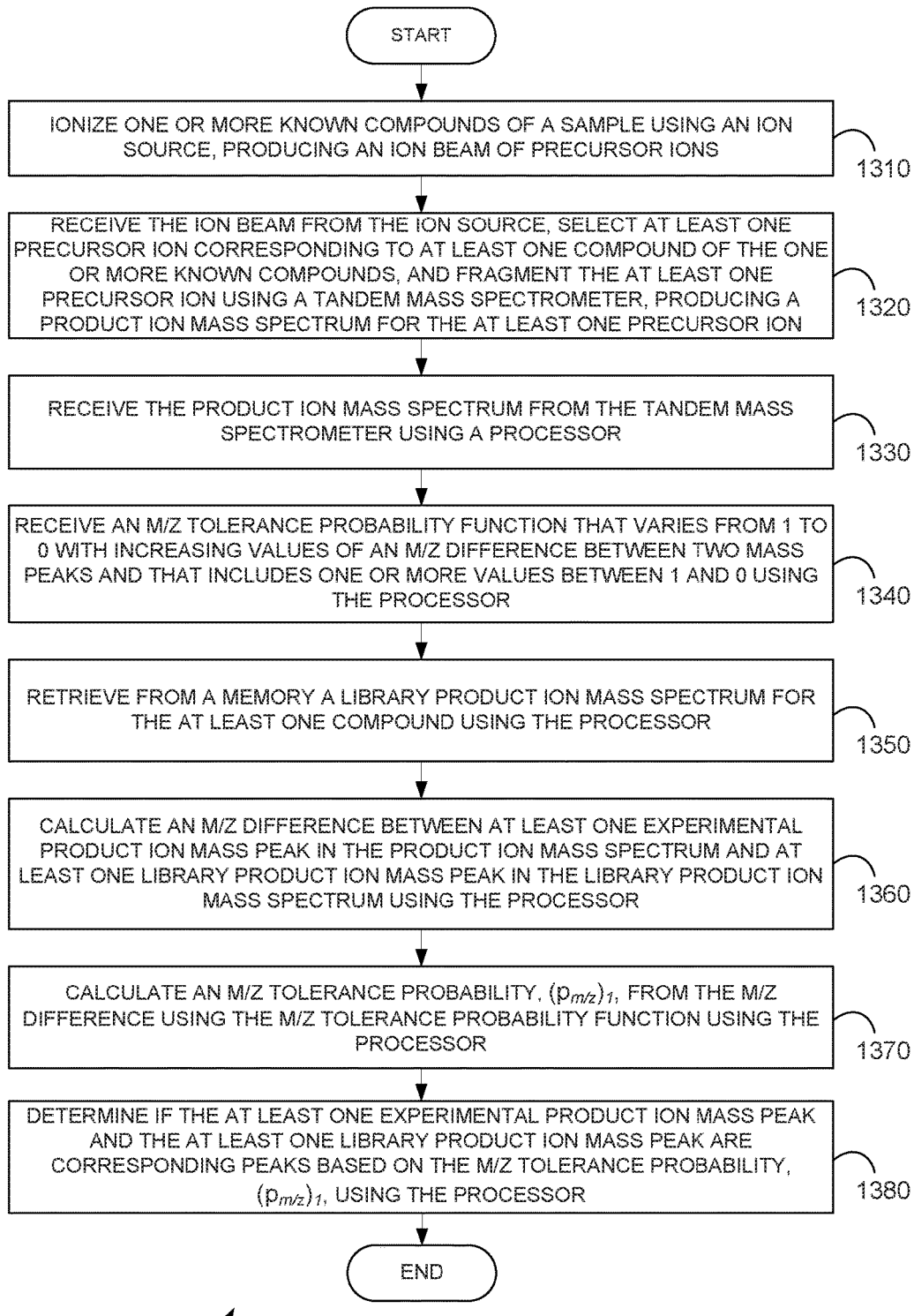
FIG. 13 is a flowchart showing a method for determining corresponding mass peaks in experimental and library product ion spectra using an m/z tolerance probability function with values between 1 and 0, in accordance with various embodiments.

FIG. 13 is a flowchart showing a method 1300 for determining corresponding mass peaks in experimental and library product ion spectra using an m/z tolerance probability function with values between 1 and 0, in accordance with various embodiments.

In step 1310 of method 1300, one or more known compounds of a sample are ionized using an ion source, producing an ion beam of precursor ions.

In step 1320, the ion beam is received from the ion source, at least one precursor ion from the ion beam corresponding to at least one compound of the one or more known compounds is selected, and the at least one precursor ion is fragmented using a tandem mass spectrometer, producing a product ion mass spectrum for the at least one precursor ion.

In step 1330, the product ion mass spectrum is received from the tandem mass spectrometer using a processor.

In step 1340, an m/z tolerance probability function that varies from 1 to 0 with increasing values of an m/z difference between two mass peaks and that includes one or more values between 1 and 0 is received using the processor.

In step 1350, a library product ion mass spectrum for the at least one compound is retrieved from a memory using the processor.

In step 1360, an m/z difference between at least one experimental product ion mass peak in the product ion mass spectrum and at least one library product ion mass peak in the library product ion mass spectrum is calculated using the processor.

In step 1370, an m/z tolerance probability, $(p_{m/z})_1$, is calculated from the m/z difference using the m/z tolerance probability function using the processor.

Finally, in step 1380, it is determined if the at least one experimental product ion mass peak and the at least one library product ion mass peak are corresponding peaks based on the m/z tolerance probability, $(p_{m/z})_1$, using the processor.

Computer Program Product for Determining Corresponding Peaks

In various embodiments, computer program products include a tangible computer-readable storage medium whose contents include a program with instructions being executed on a processor so as to perform a method for determining corresponding mass peaks in experimental and library product ion spectra using an m/z tolerance probability function with values between 1 and 0. This method is performed by a system that includes one or more distinct software modules.

Figure 14:
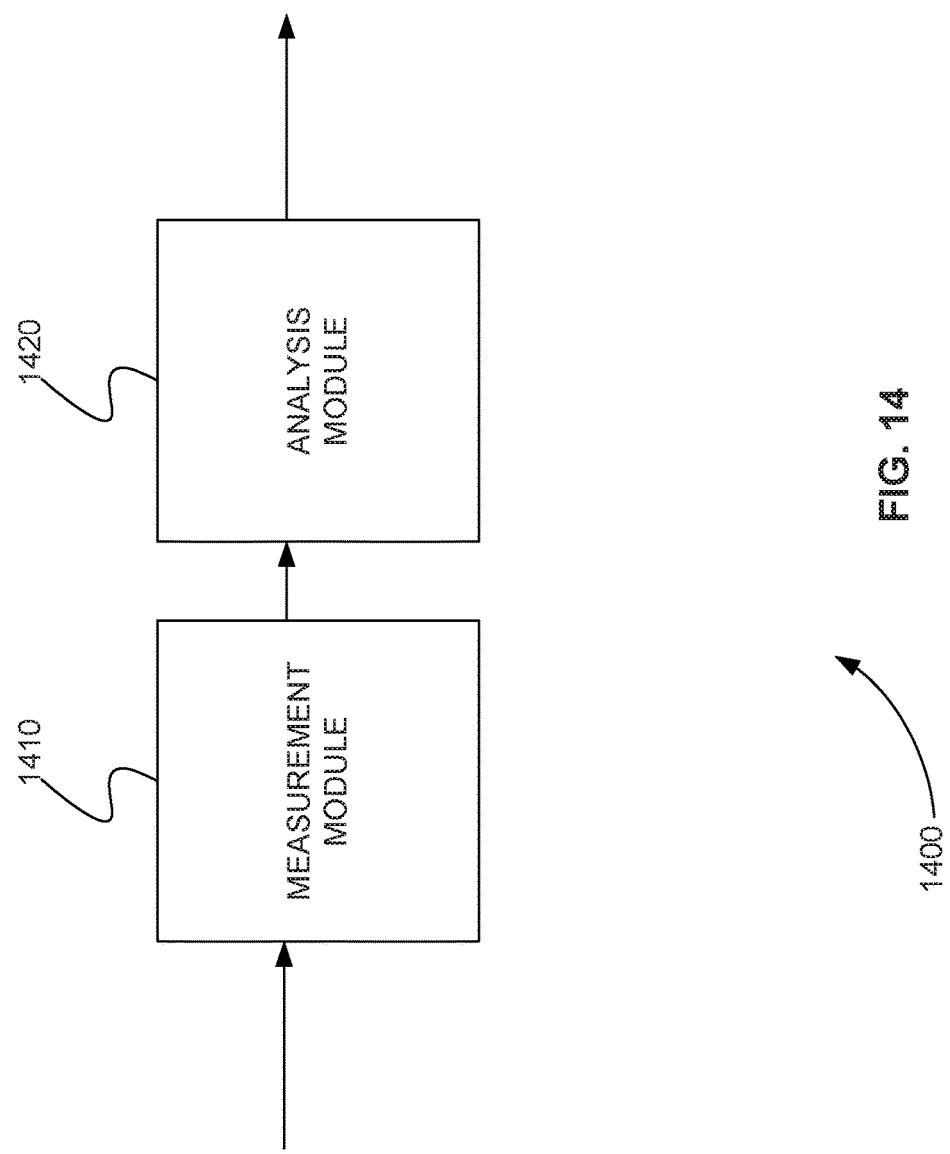
FIG. 14 is a schematic diagram of a system that includes one or more distinct software modules that performs a method for determining corresponding mass peaks in experimental and library product ion spectra using an m/z tolerance probability function with values between 1 and 0, in accordance with various embodiments.

FIG. 14 is a schematic diagram of a system 1400 that includes one or more distinct software modules that performs a method for determining corresponding mass peaks in experimental and library product ion spectra using an m/z tolerance probability function with values between 1 and 0, in accordance with various embodiments. System 1400 includes measurement module 1410 and an analysis module 1420.

Measurement module 1410 receives a product ion mass spectrum from a tandem mass spectrometer. One or more known compounds of a sample are ionized using an ion source, producing an ion beam of precursor ions. The tandem mass spectrometer receives the ion beam from the ion source, selects at least one precursor ion from the ion beam corresponding to at least one compound of the one or more known compounds, and fragments the at least one precursor ion, producing the product ion mass spectrum for the at least one precursor ion.

Analysis module 1420 receives an m/z tolerance probability function that varies from 1 to 0 with increasing values of an m/z difference between two mass peaks and that includes one or more values between 1 and 0. Analysis module 1420 retrieves from a memory a library product ion mass spectrum for the at least one compound. Analysis module 1420 calculates an m/z difference between at least one experimental product ion mass peak in the product ion mass spectrum and at least one library product ion mass peak in the library product ion mass spectrum.

Analysis module 1420 calculates an m/z tolerance probability, $(p_{m/z})_1$, from the m/z difference using the m/z tolerance probability function. Finally, analysis module 1420 determines if the at least one experimental product ion mass peak and the at least one library product ion mass peak are corresponding peaks based on the m/z tolerance probability, $(p_{m/z})_1$.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for determining corresponding mass peaks in experimental and library product ion spectra using a mass-to-charge ratio (m/z) tolerance probability function with values between 1 and 0, comprising:

an ion source that ionizes one or more known compounds of a sample, producing an ion beam of precursor ions;

a tandem mass spectrometer that receives the ion beam from the ion source and that selects at least one precursor ion from the ion beam corresponding to at least one compound of the one or more known compounds and fragments the at least one precursor ion, producing a product ion mass spectrum for the at least one precursor ion; and a processor in communication with the tandem mass spectrometer that receives the product ion mass spectrum from the tandem mass spectrometer, receives an m/z tolerance probability function that varies from 1 to 0 with increasing values of an m/z difference between two mass peaks and that includes one or more values between 1 and 0, retrieves from a memory a library product ion mass spectrum for the at least one compound, calculates an m/z difference between at least one experimental product ion mass peak in the product ion mass spectrum and at least one library product ion mass peak in the library product ion mass spectrum, calculates an m/z tolerance probability, $(p_{m/z})_1$, from the m/z difference using the m/z tolerance probability function, and determines if the at least one experimental product ion mass peak and the at least one library product ion mass peak are corresponding peaks based on the m/z tolerance probability, $(p_{m/z})_1$.

2. The system of claim 1, wherein the processor further calculates a score for a comparison of the product ion mass spectrum and the library product ion mass spectrum that includes calculating a product of the m/z tolerance probability, $(p_{m/z})_1$, an intensity of the at least one experimental product ion mass peak, $U_1$, and an intensity of the at least one library product ion mass peak, $L_1$.

3. The system of claim 2, wherein the processor calculates the score using $(p_{m/z})_1$, $U_1$, and $L_1$ and any other $(p_{m/z})_i$, $U_i$, and $L_i$ according to:

$$\text{score} = 100\% \times \frac{\left(\sum (p_{m/z})_i U_i L_i\right)^2}{\sum U_i U_i \times \sum L_i L_i}$$

where $U_i$ is the intensity of ith unknown or experimental peak, $L_i$ is the intensity of ith library peak, and $(p_{m/z})_i$ is probability that two peaks with intensities $U_i$ and $L_i$ are corresponding peaks.

4. The system of claim 3, wherein $U_i$ and $L_i$ include a weighting factor or are transformed mathematically from the original values measured by the mass spectrometer.

5. The system of claim 1, wherein the processor further receives an intensity ratio threshold probability function that varies from 1 to 0 with increasing values of a ratio of intensities of two mass peaks and that includes one or more values between 1 and 0, calculates an intensity ratio from an intensity of the at least one experimental product ion mass peak and an intensity of the at least one library product ion mass peak, calculates an intensity threshold probability, $(p_{ratio})_1$, from the intensity ratio using the intensity ratio threshold probability function, and modifies an intensity, $U_1$, of the at least one experimental product ion mass peak or an intensity, $L_1$, of the at least one library product ion mass peak based on the intensity threshold probability, $(p_{ratio})_1$.

6. The system of claim 5, wherein the processor modifies the intensity, $L_1$, of the at least one library product ion mass peak according to modified $L_1 = L_1 + (p_{ratio})_1 \times (U_1 - L_1)$.

7. The system of claim 6, wherein the processor further calculates a score for a comparison of the product ion mass spectrum and the library product ion mass spectrum using modified $L_1$, and any other modified $L_i$ according to:

$$\text{score} = 100\% \times \frac{\left(\sum (p_{m/z})_i U_i \text{ modified} L_i\right)^2}{\sum U_i U_i \times \sum \text{modified} L_i \text{modified} L_i}$$

where $U_i$ is the intensity of ith unknown or experimental peak, $(p_{m/z})_i$ is probability that two peaks with intensities $U_i$ and $L_i$ are corresponding peaks, and modified $L_i$ is calculated according to modified $L_i = L_i (p_{ratio})_i \times (U_i - L_i)$ where $L_i$ is the intensity of ith library peak.

8. The system of claim 5, wherein the processor further calculates an overall probability, $(p_{match})_1$, that the at least one experimental product ion mass peak and the at least one library product ion mass peak match by combining the m/z tolerance probability, $(p_{m/z})_1$, and the intensity threshold probability, $(p_{ratio})_1$.

9. A method for determining corresponding mass peaks in experimental and library product ion spectra using a mass-to-charge ratio (m/z) tolerance probability function with values between 1 and 0, comprising:

ionizing one or more known compounds of a sample using an ion source, producing an ion beam of precursor ions;

receiving the ion beam from the ion source, selecting at least one precursor ion from the ion beam corresponding to at least one compound of the one or more known compounds, and fragmenting the at least one precursor ion using a tandem mass spectrometer, producing a product ion mass spectrum for the at least one precursor ion;

receiving the product ion mass spectrum from the tandem mass spectrometer using a processor;

receiving an m/z tolerance probability function that varies from 1 to 0 with increasing values of an m/z difference between two mass peaks and that includes one or more values between 1 and 0 using the processor;

retrieving from a memory a library product ion mass spectrum for the at least one compound using the processor;

calculating an m/z difference between at least one experimental product ion mass peak in the product ion mass spectrum and at least one library product ion mass peak in the library product ion mass spectrum using the processor;

calculating an m/z tolerance probability, $(p_{m/z})_1$, from the m/z difference using the m/z tolerance probability function using the processor; and determining if the at least one experimental product ion mass peak and the at least one library product ion mass peak are corresponding peaks based on the m/z tolerance probability, $(p_{m/z})_1$, using the processor.

10. The method of claim 9, further comprising calculating a score for a comparison of the product ion mass spectrum and the library product ion mass spectrum that includes calculating a product of the m/z tolerance probability, $(p_{m/z})_1$, an intensity of the at least one experimental product ion mass peak, $U_1$, and an intensity of the at least one library product ion mass peak, $L_1$, using the processor.

11. The method of claim 10, wherein the score is calculated using $(p_{m/z})_1$, $U_1$, and $L_1$ and any other $(p_{m/z})_i$, $U_i$, and $L_i$ according to:

$$\text{score} = 100\% \times \frac{\left(\sum (p_{m/z})_i U_i L_i\right)^2}{\sum U_i U_i \times \sum L_i L_i}$$

where $U_i$ is the intensity of ith unknown or experimental peak, $L_i$ is the intensity of ith library peak, and $(p_{m/z})_i$ is probability that two peaks with intensities $U_i$ and $L_i$ are corresponding peaks.

12. The method of claim 9, further comprising receiving an intensity ratio threshold probability function that varies from 1 to 0 with increasing values of a ratio of intensities of two mass peaks and that includes one or more values between 1 and 0 using the processor, calculating an intensity ratio from an intensity of the at least one experimental product ion mass peak and an intensity of the at least one library product ion mass peak using the processor, calculating an intensity threshold probability, $(p_{ratio})_1$, from the intensity ratio using the intensity ratio threshold probability function using the processor, and modifying an intensity, $U_1$, of the at least one experimental product ion mass peak or an intensity, $L_1$, of the at least one library product ion mass peak based on the intensity threshold probability, $(p_{ratio})_1$, using the processor.

13. The method of claim 12, wherein the intensity, $L_1$, of the at least one library product ion mass peak is modified according to $$\text{modified } L_1 = L_1 (p_{ratio})_1 \times (U_1 - L_1).$$

14. The method of claim 13, further comprising calculating a score for a comparison of the product ion mass spectrum and the library product ion mass spectrum using modified $L_1$, and any other modified $L_i$ according to:

$$\text{score} = 100\% \times \frac{\left(\sum (p_{m/z})_i U_i \text{modified} L_i\right)^2}{\sum U_i U_i \times \sum \text{modified} L_i \text{modified} L_i}$$

where $U_i$ is the intensity of ith unknown or experimental peak, $(p_{m/z})_i$ is probability that two peaks with intensities $U_i$ and $L_i$ are corresponding peaks, and modified $L_i$ is calculated according to $$\text{modified } L_i = L_i (p_{ratio})_i \times (U_i - L_i)$$

where $L_i$ is the intensity of ith library peak.

15. A computer program product, comprising a non-transitory and tangible computer-readable storage medium whose contents include a program with instructions being executed on a processor so as to perform a method for determining corresponding mass peaks in experimental and library product ion spectra using a mass-to-charge ratio (m/z) tolerance probability function with values between 1 and 0, the method comprising:

providing a system, wherein the system comprises one or more distinct software modules, and wherein the distinct software modules comprise a measurement module and an analysis module;

receiving a product ion mass spectrum from a tandem mass spectrometer using the measurement module, wherein one or more known compounds of a sample are ionized using an ion source, producing an ion beam of precursor ions and wherein the tandem mass spectrometer receives the ion beam from the ion source, selects at least one precursor ion from the ion beam corresponding to at least one compound of the one or more known compounds, and fragments the at least one precursor ion, producing the product ion mass spectrum for the at least one precursor ion;

receiving an m/z tolerance probability function that varies from 1 to 0 with increasing values of an m/z difference between two mass peaks and that includes one or more values between 1 and 0 using the analysis module;

retrieving from a memory a library product ion mass spectrum for the at least one compound using the analysis module;

calculating an m/z difference between at least one experimental product ion mass peak in the product ion mass spectrum and at least one library product ion mass peak in the library product ion mass spectrum using the analysis module;

calculating an m/z tolerance probability, $(p_{m/z})_1$, from the m/z difference using the m/z tolerance probability function using the analysis module; and determining if the at least one experimental product ion mass peak and the at least one library product ion mass peak are corresponding peaks based on the m/z tolerance probability, $(p_{m/z})_1$, using the analysis module.

\* \* \* \* \*